US009603849B2

(12) United States Patent
Ratti et al.

(10) Patent No.: US 9,603,849 B2
(45) Date of Patent: Mar. 28, 2017

(54) USES OF ORVEPITANT

(71) Applicant: NERRE THERAPEUTICS LIMITED, Stevenage Herts (GB)

(72) Inventors: Emiliangelo Ratti, Stevenage (GB); Michael Trower, Stevenage (GB)

(73) Assignee: NERRE THERAPEUTICS LIMITED, Stevenage Herts (GB)

( * ) Notice: Subject to any disclaimer, the term of this patent is extended or adjusted under 35 U.S.C. 154(b) by 0 days.

(21) Appl. No.: 14/426,620

(22) PCT Filed: Oct. 9, 2013

(86) PCT No.: PCT/EP2013/071093
§ 371 (c)(1),
(2) Date: Mar. 6, 2015

(87) PCT Pub. No.: WO2014/057003
PCT Pub. Date: Apr. 17, 2014

(65) Prior Publication Data
US 2015/0238486 A1 Aug. 27, 2015

Related U.S. Application Data

(60) Provisional application No. 61/712,499, filed on Oct. 11, 2012.

(51) Int. Cl.
*A61K 31/4985* (2006.01)
*A61K 31/495* (2006.01)

(52) U.S. Cl.
CPC ........ *A61K 31/4985* (2013.01); *A61K 31/495* (2013.01)

(58) Field of Classification Search
None
See application file for complete search history.

(56) References Cited

U.S. PATENT DOCUMENTS

| 5,679,360 A | 10/1997 | Lacharriere et al. |
| 6,203,803 B1 | 3/2001 | Charriere et al. |
| 8,906,951 B1 | 12/2014 | Zhang et al. |

FOREIGN PATENT DOCUMENTS

| GB | WO 2009124996 A1 * | 10/2009 | ........... C07D 487/04 |
| WO | 03026658 A1 | 4/2003 | |

(Continued)

OTHER PUBLICATIONS

Wallengren, "Topical aprepitant in clinical and experimental pruritus," Arch Dermatol. Aug. 2012;148(8):957-9.

(Continued)

*Primary Examiner* — San-Ming Hui
*Assistant Examiner* — Andrew Lee
(74) *Attorney, Agent, or Firm* — Silvia Salvadori, P.C.; Silvia Salvadori

(57) ABSTRACT

This invention relates to the new use of the compound (I) or pharmaceutically acceptable salts thereof and pharmaceutical compositions containing it for the treatment of pruritus and to combinations for such a use.

(Continued)

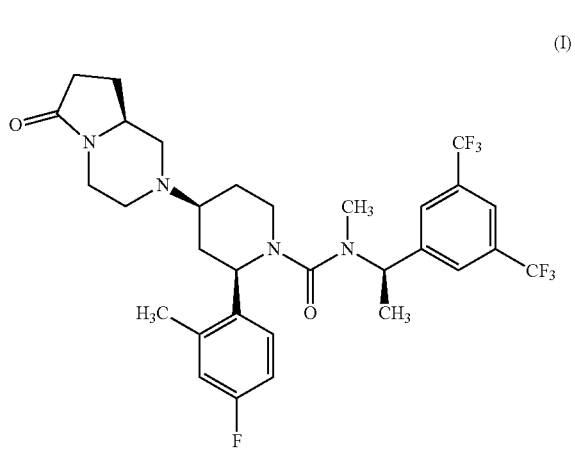

(I)

5 Claims, 2 Drawing Sheets

(56) References Cited

FOREIGN PATENT DOCUMENTS

WO    03066635       8/2003
WO    2013124286 A1  8/2013

OTHER PUBLICATIONS

Williams-Fritze et al., "Maropitant citrate for treatment of ulcerative dermatitis in mice with a C57BL/6 background," J Am Assoc Lab Anim Sci. Mar. 2011;50(2):221-6.
Yamaoka et al., "Rapid changes in substance P signaling and neutral endopeptidase induced by skin-scratching stimulation in mice," J Dermatol Sci. Nov. 2007;48(2):123-32.
Booken et al, "Oral aprepitant in the therapy of refractory pruritus in erythrodermic cutaneous T-cell lymphoma," Br J Dermatol. Mar. 2011;164(3):665-7.
Booken et al., "Oral aprepitant in the therapy of refractory pruritus in erythrodermic cutaneous T-cell lymphoma," Br J Dermatol. Mar. 2011:164(3):665-7.
Borici et al., "Cutaneous responses to substance P and calcitonin gene-related peptide in chronic urticaria: the effect of cetirizine and dimethindene," Allergy. Jan. 1999;54(1):46-56.
Burbach et al., "The neurosensory tachykinins substance P and neurokinin A directly induce keratinocyte nerve growth factor," J Invest Dermatol. Nov. 2001;117(5):1075-82.
Chiang et al., "Cancer and itch," Semin Cutan Med Surg. Jun. 2011;30(2):107-12.
Divito et al., "Role of neurokinin-1 receptor in the initiation and maintenance of skin chronic inflammatory diseases," Immunol Res. Aug. 2011;50(2-3):195-201.
Duval et al., "Aprepitant as an Antipruritic Agent?," N Engl J Med. Oct. 1, 2009;361(14):1415-6.
Eberz, et al., "Substance P-induced histamine release in human cutaneous mast cells," J Invest Dermatol. Jun. 1987;88(6):682-5.
Editors: Granstein et al., "Neuroimmunology of the Skin," 2009.
Eedy et al., "Neuropeptides in psoriasis: an immunocytochemical and radioimmunoassay study," J Invest Dermatol. Apr. 1991;96(4):434-8.
Fantini et al., "Substance P levels are decreased in lesional skin of atopic dermatitis," Exp Dermatol. Oct. 1992;1(3):127-8.
Forsythe et al., "The mast cell-nerve functional unit: a key component of physiologic and pathophysiologic responses," Chem Immunol Allergy. 2012;98:196-221.
Gerber et al., "More on aprepitant for erlotinib-induced pruritus," N Engl J Med. Feb. 3, 2011;364(5):486-7.
Gerber et al., "Preliminary evidence for a role of mast cells in epidermal growth factor receptor inhibitor-induced pruritus," J Am Acad Dermatol. Jul. 2010;63(1):163-5.
Grundmann, et al., "Chronic pruritus: clinics and treatment," Ann Deramtol. Feb. 2011;23(1):1-11.
Hägermark et al., "Flare and itch induced by substance P in human skin," J Invest Dermatol. Oct. 1978;71(4):233-5.
Hartschuh et al., "Peptidergic (neurotensin, VIP, substance P) nerve fibres in the skin. Immunohistochemical evidence of an involvement of neuropeptides in nociception, pruritus and inflammation," Br J Dermatol. Jul. 1983;109 Suppl 25:14-7.
Hon, et al., "Pathophysiology of nocturnal scratching in childhood atopic dermatitis: the role of brain-derived neurotrophic factor and substance P.," Br J Dermatol. Nov. 2007;157(5):922-5.
Hossen et al., "Role of substance P on histamine H(3) antagonist-induced scratching behavior in mice," J Pharmacol Sci. Apr. 2006;100(4):297-302.
Ikoma et al., "The neurobiology of itch," Nat Rev Neurosci. Jul. 2006;7(7):535-47.
Inagaki et al., "Depletion of substance P, a mechanism for inhibition of mouse scratching behavior by tacrolimus," Eur J Pharmacol. Jan. 25, 2010;626(2-3):283-9.
Kawana et al., "Role of substance P in stress-derived degranulation of dermal mast cells in mice," J Dermatol Sci. Apr. 2006;42(1):47-54.
Kulka et al., "Neuropeptides activate human mast cell degranulation and chemokine production," Immunology. Mar. 2008;123(3):398-410.
Kumagai et al., "Effects of stress memory by fear conditioning on nerve-mast cell circuit in skin," J Dermatol. Jun. 2011;38(6):553-61.
Lee et al., "Korean red ginseng extract ameliorates skin lesions in NC/Nga mice: An atopic dermatitis model," J Ethnopharmacol. Jan. 27, 2011;133(2)1310-7.
Levêque D., "Aprepitant for Erlotinib-Induced Pruritus," N Engl J Med. Oct. 21, 2010;363(17):1680-1.
Maintz et al., "Neuropeptide blood levels correlate with mast cell load in patients with mastocytosis," Allergy. Jul. 2011;66(7):862-9.
Mir et al., "Aprepitant for pruritus: drug-drug interactions matter," Lancet Oncol. Oct. 2012;13(10):964-5.
Mir et al., "More on aprepitant for erlotinib-induced pruritus," N Engl J Med. Feb. 3, 2011;364(5):487.
Murota, et al., "Artemin causes hypersensitivity to warm sensation, mimicking warmth-provoked pruritus in atopic dermatitis," J Allergy Clin Immunol. Sep. 2012;130(3):671-682.e4.
Potenzieri et al., "Basic mechanisms of itch," Clin Exp Allergy. Jan. 2012;42(1):8-19.
Raap et al., "Pathophysiology of itch and new treatments," Curr Opin Allergy Clin Immunol. Oct. 2011;11(5):420-7.
Salomon et al., "The role role of selected neuropeptides in pathogenesis of atopic dermatitis," J Eur Acad Dermatol Venereol. Feb. 2008;22(2):223-8.
Santini et al., "Aprepitant for management of severe pruritus related to biological cancer treatments: a pilot study," Lancet Oncol. Oct. 2012;13(10):1020-4.
Santini et al., "Aprepitant is active in biological therapies induced severe pruritus: final results of the Italian proof of concept study," Poster from American Society of Clinical Oncology (2011).
Stander et al,, "Medical treatment of pruritus," Expert Opin Emerg Drugs. Sep. 2012;17(3):335-45.
Stander et al., "Targeting the Neurokinin Receptor 1 with Aprepitant: A Novel Antipruritic Stratetgy," PloS One, Jun. 2010, vol. 5, Issue 6 pp. e10968 pp. 1-5.
Staniek et al., "Modulation of cutaneous SP receptors in atopic dermatitis after UVA irradiation," Acta Derm Venereol. Mar. 1998;78(2):92-4.
Sugiura et al, "Density and fine structure of peripheral nerves in various skin lesions of atopic dermatitis," Arch Dermatol Res. Feb. 1997;289(3):125-31.

(56) References Cited

OTHER PUBLICATIONS

Tedeschi, et al., "No evidence of increased serum substance P levels in chronic urticaria patients with and without demonstrable circulating vasoactive factors," Clin Exp Dermatol. Mar. 2005;30(2):171-5.
Tey et al., "Pruritus," Pruritus. 2011. pp. 1-12.
Tey et al., "Targeted treatment of pruritus: a look into the future," British Journal of Dermatology, Jul. 2011, 165, pp. 5-17.
Thomsen et al., "Experimental itch in sodium lauryl sulphate-inflamed and normal skin in humans: a randomized, double-blind, placebo-controlled study of histamine and other inducers of itch," Br J Dermatol. May 2002;146(5):792-800.
Torres et al., "Aprepitant: Evidence of its effectiveness in patients with refractory pruritus continues," J Am Acad Dermatol. Jan. 2012;66(1):e14-5.
Toyoda, et al., "Nerve growth factor and substance P are useful plasma markers of disease activity in atopic dermatitis," Br J Dermatol. Jul. 2002;147(1):71-9.
Trivedi, et al., "Serum concentrations of substance P in cholestasis," Ann Hepatol. Apr.-Jun. 2010;9(2):177-80.
Ueda et al., "A new chronic itch model accompanied by skin lesions in hairless mice," Int Immunopharmacol. Oct. 2006;6(10):1609-15.

Vincenzi et al., "Aprepitant against pruritus in patients with solid tumours," Support Care Cancer. Sep. 2010;18(9):1229-30.
Vincenzi et al., "Aprepitant for Erlotinib-Induced Pruritus," N Engl J Med. Jul. 22, 2010;363(4):397-8.
Wallengren, "Substance P antagonist inhibits immediate and delayed type cutaneous hypersensitivity reactions," Br J Dermatol. Apr. 1991;124(4):324-8.
Stander et al., "Targeting the Neurokinin Receptor 1 with Aprepitant: A Novel Antipruritic Strategy", PLOS ONE, vol. 5, No. 6, Jan. 1, 2010, pp. e10968-e10968.
Torres et al., "Aprepitant: Evidence of its effectiveness in patients with refractory pruritus continues", Journal of American Academy of Dermatology, vol. 66 No. 1, Jan. 2012 pp. e14-e15.
Santini et al., "Aprepitant for management of severe pruritus related to biological cancer treatments: a pilot study", The Lancet Oncology, vol. 13, No. 10, Sep. 18, 2012.
Grundmann et al., "Chronic Pruritus: Clinics and Treatment", Annals of Dermatology, vol. 23, No. 1, Jan. 1, 2011.
Williams-Fritze et al., "Maropitant Citrate for Treatment of Ulcerative Dermatitis in MIce iwth a C57BL/6 Background", Mar. 1, 2011.
International Search Report and Written Opinion of PCT/EP2013/071093 mailed on Dec. 4, 2013.

* cited by examiner

USES OF ORVEPITANT

This application is a U.S. national stage of PCT/EP2013/071093 filed on 9 Oct. 2013, which claims priority to and the benefit of U.S. Provisional Application No. 61/712,499 filed on 11 Oct. 2012, the contents of which are incorporated herein by reference in their entireties.

FIELD OF THE INVENTION

This invention relates to the new use of the compound 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof and pharmaceutical compositions containing it for the treatment of pruritus and to combinations for such a use.

BACKGROUND OF THE INVENTION

WO2003/066635 describes a number of diazabicycle derivatives having NK1 antagonist activity, including the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (otherwise known as orvepitant).

Orvepitant, otherwise known as 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide has the following chemical structure (I).

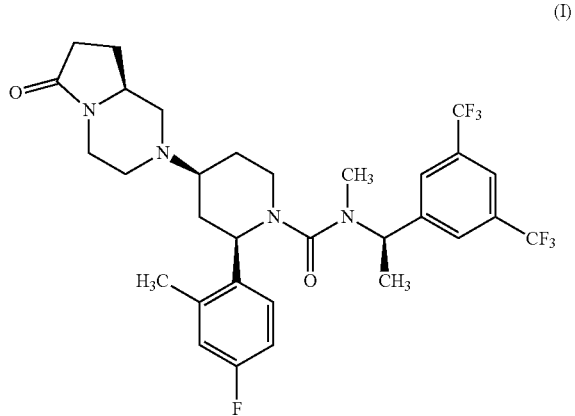 [SMILES: Cc1cc(F)ccc1[C@H]1C[C@@H](N2CCN3C(=O)CC[C@H]3C2)CCN1C(=O)N(C)[C@H](C)c1cc(C(F)(F)F)cc(C(F)(F)F)c1]

(I)

Hereinafter any reference to orvepitant refers to the compound (I).

Orvepitant may also be known as:

CAS Index name 1-Piperidinecarboxamide, N-[(1R)-1-[3,5-bis(trifluoromethyl)phenyl]ethyl]-2-(4-fluoro-2-methylphenyl)-4-[(8aS)-hexahydro-6-oxopyrrolo[1,2-a]pyrazin-2(1H)-yl]-N-methyl-, (2R,4S)

and

IUPAC name:

(2R,4S)—N-{(1R)-1-[3,5-bis(trifluoromethyl)phenyl]ethyl}-2-(4-fluoro-2-methylphenyl)-N-methyl-4-[(8aS)-6-oxohexahydropyrrolo[1,2-a]pyrazin-2(1H)-yl]-1-piperidinecarboxamide.

A preferred salt of the compound(I) is its hydrochloride salt which is otherwise known as orvepitant hydrochloride.

A further preferred salt of the compound(I) is its maleate salt which is otherwise known as orvepitant maleate.

WO2009/124996 describes a new crystalline form of orvepitant maleate namely anhydrous crystalline form (Form1).

The compound (I), pharmaceutically acceptable salts thereof are described in the aforementioned specifications as antagonists of tachykinin receptors, including substance P (SP) and other neurokinin receptors, both in vitro and in vivo and are thus of use in the treatment of conditions mediated by tachykinins, including SP and other neurokinins.

Particularly, the compound (I), and pharmaceutically acceptable salts or solvates thereof are described as useful in the treatment of central nervous system (CNS) disorders.

We have now surprisingly found that the compound (I) or pharmaceutically acceptable salts thereof are also useful in the treatment of pruritus.

Particularly, we have found that the compound (I) or pharmaceutically acceptable salts thereof are useful in the treatment of chronic pruritus.

Pruritus can be defined as an unpleasant sensation that evokes the desire to scratch.

Thus according to International Classification of Diseases (ICD-10-CM) pruritus is defined as intense itching sensation that produces the urge to rub or scratch the skin to obtain relief.

Pruritus is a physiological perception within the sensory neuronal network in the skin which, along with pain and physical or mechanical stimuli, serves as a warning system against potential bodily threats and it is an integral part of patient's symptoms in numerous dermatological and systemic diseases. Pruritus can have a dramatic impact on quality of life and can worsen the general condition and capacity of the patient considerably.

Only in the past decade has pruritus received attention in scientific research and despite the significant advancements made in understanding this condition, there are still many underlying mechanisms in its pathophysiology that remain unknown (Ständer S et al. *Journal of the Germany Society of Dermatology* (2011), 9:456-463).

In recent years, pruritus has been defined as an autonomous, pain-independent sensation, and itch-specific neurons, mediators, spinal neurons, and cortical areas have been identified.

Pruritus is mediated by free nerve endings of non-myelinated nerve fibres that are located at the dermoepidermal junction and within the epidermis. For a number of diseases that involve itching, such as atopic dermatitis, prurigo nodularis, and allergic contact dermatitis, it has been suggested that the increased production and release of "nerve growth factor" (NGF) from resident skin cells such as keratinocytes or mast cells leads to an increase in intraepidermal "itch fibres" in the skin possibly leading to the exacerbation of pruritus (Ikoma A et al. *Nat Rev Neuroscience* (2006), 7(7): 535-547).

Along with the nerve fibres, mast cells in the skin also play a central role in mediating pruritus. Mast cells can release numerous biologically active mediators as a result of specific (receptor-mediated) or non-specific (e.g., via mechanical or chemical) stimuli (Metz and Maurer. *Trends Immunol* (2007), 28(5):234-241). Some of these mast cell products are characterized by their potent itch-inducing effect. Examples of mast cells products include histamine, protease, lipid mediators such as Leukotriene B4 and prostaglandins.

There are also a few substances that either cause pruritus without directly affecting nerve fibres or that mediate pruritus indirectly through activation of skin mast cells. Although these are broadly referred to as histamine liberators, the activation of mast cells as described above can also lead to the release of other pruritus-inducing substances. Among the most relevant mast cell activators in pruritic diseases are neuropeptides such as vasoactive intestinal peptide (VIP), calcitonin gene-related peptide (CGRP) and SP.

Particularly, SP is hypothesised to induce itch, following its release from sensory nerves, by activation of dermal mast cells and other cell types (including cells of the immune system) resulting in the liberation of histamine (mast cells) and other pro-inflammatory mediators (Divito S J et al. *Immunol Res* (2011), 50(2-3):195-201). Mast cells have been shown to accumulate in the lesional skin of cancer patients treated with the epidermal growth factor receptor inhibitor erlotinib and it has been proposed that the activation of these mast cells by SP accounts for the pruritus experienced by subjects administered such epidermal growth factor receptor inhibitors (Gerber P A et al. *J Am Acad Dermatol* (2010), 63(1):163-5; *N Engl J Med* (2011), 364(5):486-7). In mice there is some evidence that SP driven pruritus also involves a non-histamine/non-mast cell dependent mechanism since SP induced scratching is neither inhibited by anti-histamines nor in mast cell deficient animals. Skin-scratching is a commonly seen behaviour in patients with pruritus which often exacerbates original lesions. In a mouse model, after skin-scratching stimulation, mast cells significantly de-granulated within several minutes with SP-immunoreactive nerve fibres disappearing immediately from sensory nerve fibres, indicating the quick secretion and depletion of SP; blockade by a NK-1 antagonist suppressed these scratching-induced decreases in SP-immunoreactive nerve fibres (Yamaoka et al. *J Dermatol Sci* (2007), 48(2):123-132).

It has been also demonstrated that intradermal injection of SP into skin of both animals (Andoh T et al. *The Journal of Pharmacology and Experimental Therapeutics* (1998), 286 (3):1140-1145) and humans (Thomsen J S et al. *British J Dermatology* (2002), 146(5):792-800) induces itching and scratching. Despite SP being an important neuropeptide mediating pruritus, the clinical efficacy of NK-1 antagonists for the treatment of pruritus has yet to be fully evaluated and elucidated (Tey H L & Yosipovitch G. *British Journal Pharmacology* (2011), 165:5-17). The symptom of chronic itch represents a worldwide burden in the community as well as in specific populations (Weisshaar E & Dalgard F. *Acta Derm. Venereol* (2009), 89:339-350). It is desirable to translate these recent improvements in the understanding of the pathophysiology of pruritus into new therapeutics.

Therapeutic options for pruritus are limited and treatment is sub-optimal, there is a requirement for new and effective anti-pruritic drugs to meet the significant unmet need.

Classification of Pruritus

Because pruritus occurs in many diseases of different etiologies, various classification systems for pruritus exist. Pruritus has been recently reclassified by the International Forum for the Study of Itch (IFSI) in 2007 (Ständer S et al. *Acta Derm Venereol* (2007), 87:291-294).

According to this classification system, pruritus can be distinguished as acute and chronic, with the latter defined as pruritus lasting 6 or more weeks and it has been classified into the following groups.

Group I. The first group is named pruritus on primary diseased, inflamed skin.

Many skin diseases are accompanied by itch. They comprise inflammatory, infectious, or autoimmune cutaneous diseases, genodermatoses, drug reactions, dermatoses of pregnancy and skin lymphomas, all of which lead to specific skin changes described elsewhere.

The underlying diseases according to Group I include Category I.

Category I Pruritus associated with or due to a dermatological disorder, disease or condition such as:

Inflammatory dermatoses including atopic dermatitis/eczema, psoriasis, irritant/contact dermatitis, irritant/contact eczema, urticaria, dry skin, adverse drug reactions, scars, pruritus ani, pruritus scroti, pruritus vulvae and 'invisible dermatoses';

Infectious dermatoses including mycotic, bacterial and viral infections and folliculitis, scabies, pediculosis, arthropod reactions and insect bites;

Autoimmune dermatoses including bullous dermatoses, especially dermatitis herpetiformis Duhring, bullous pemphigoid and dermatomyositis;

Genodermatoses including Darier's disease, Hailey-Hailey disease, ichthyoses, Sjögren-Larsson syndrome and epidermolysis bullosa pruriginosa;

Dermatoses of pregnancy including polymorphic eruption of pregnancy, pemphigoid gestationis and prurigo gestationis;

Neoplasms including cutaneous T-cell-lymphoma (especially erythrodermic variants and Sézary syndrome and mycosis fungoides), cutaneous B-cell lymphoma and leukaemic infiltrates of the skin.

Group II. Pruritus on primary non-diseased, non-inflamed skin.

Patients with pruritic diseases of systemic, neurological or psychosomatic/psychiatric origin experience pruritus without any skin lesions except for possible secondary scratch lesions. Systemic diseases leading to itch include endocrine and metabolic disorders, infections, haematological and lymphoproliferative diseases, solid neoplasms and drug-induced pruritus.

The underlying diseases according to Group II include Category II-IV.

Category II. Pruritus associated with or due to a systemic disorder, disease or condition such as:

Endocrine and metabolic diseases including chronic renal failure, liver diseases with or without cholestasis, hyperthyroidism, malabsorption, perimenopausal pruritus and diabetes mellitus;

Infectious diseases including HIV-infection, HCV infection, chicken-pox, helminthosis and parasitosis;

Haematological and lymphoproliferative diseases including iron deficiency, polycythaemia vera, Hodgkin's disease, Non-Hodgkin's lymphoma and plasmocytoma;

Visceral neoplasms including solid tumours of the cervix, prostate, or colon and carcinoid syndrome;

Pregnancy including pruritus gravidarum with and without cholestasis;

Drug-induced pruritus such as opioids, ACE-inhibitors, amiodarone, hydrochlorothiazid, estrogens, simvastatin, hydroxyethyl starch, allopurinol; section also includes chemotherapy-induced pruritus as a result of treatment with agents such as kinase inhibitors (for example epidermal growth factor receptor inhibitors like erlotinib and cetuximab).

Category III. Pruritus associated with or due to a neurogenic disorder, disease or condition such as:

Neurogenic origin (without neuronal damage) including hepatic itch with increased endogenous μ-opioids (dis-inhibition of itch);

Neuropathic diseases (neuronal damage causes itch) including multiple sclerosis, neoplasms, abscesses, cerebral or spinal infarcts, brachioradial pruritus, nostalgia paresthetica, post-herpetic neuralgia, vulvodynia and small fibre neuropathy.

Category IV. Pruritus associated with or due to a somatoform disorder, disease or condition such as psychiatric/psychosomatic diseases including depression, anxiety disorders, obsessive-compulsive disorders, schizophrenia, tactile hallucinosis and fatigue.

Group III. Pruritus presenting with severe chronic secondary scratch lesions.

Chronic pruritus frequently leads to mechanical reactions, such as scratching, rubbing or pinching. Scratching may induce variable damage of the skin, presenting as excoriations, crusts, lichenification, papules and nodules. These lesions may resolve leaving hyper- or hypo-pigmentation and atrophic scars of the skin. Several lesions in different stages and sizes may co-exist in patients with chronic pruritus. Some of these clinical manifestations are summarized using terms such as lichen simplex chronicus, lichen Vidal, lichen amyloidosus, macular amyloidosus, and prurigo nodularis. All of these represent secondary acquired lesions induced by chronic scratching.

The underlying origin may be either a skin or systematic diseases in Category I to IV.

The following categories have been also identified:

Category V. Pruritus associated with overlapping of disorders, diseases or conditions described in Categories I to IV.

Category VI. Pruritus associated with or due to an unknown disorder, disease or condition.

SUMMARY OF THE INVENTION

The solution provided by the present invention is the use of the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (otherwise known as orvepitant) having the following chemical structure (I)

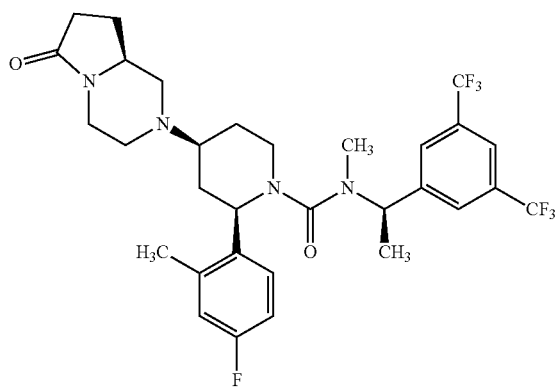

(I)

or pharmaceutically acceptable salts thereof in the treatment of pruritus.

In a first aspect thereof, the invention provides the use of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt thereof for the manufacture of a medicament for the treatment of pruritus.

In a further aspect thereof, the invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt thereof, for use in the treatment of pruritus.

In a yet further aspect, the invention provides a method of treatment of pruritus which comprises administering to a human in need thereof an effective amount 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt thereof.

In another aspect the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt thereof for use in the treatment of pruritus.

In another embodiment, the maleate salt of orvepitant is utilized in the treatment of pruritus.

In a further embodiment, orvepitant maleate Form 1 is utilized in the treatment of pruritus.

DETAILED DESCRIPTION OF THE INVENTION

Figure 1:
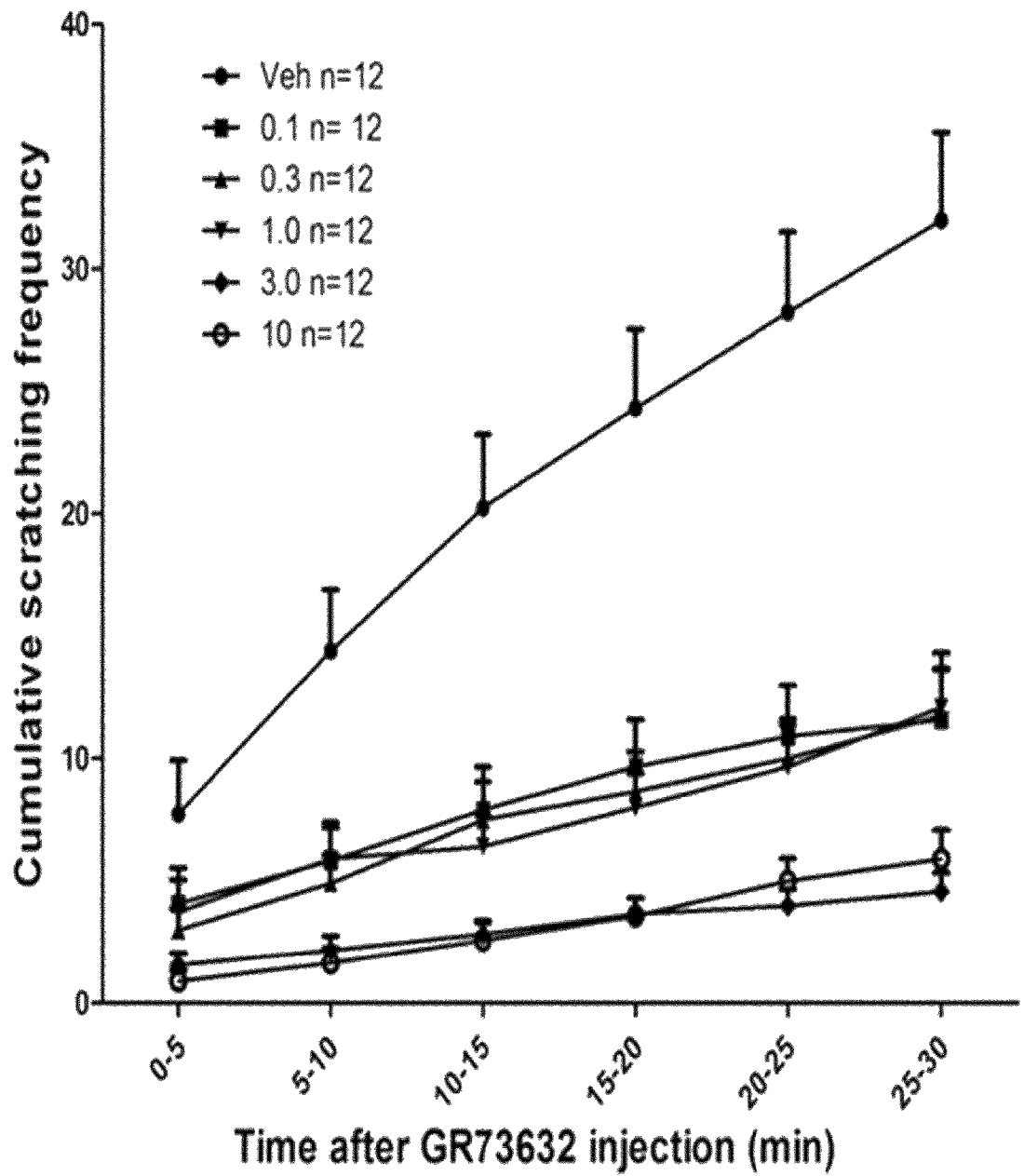
FIG. 1. Cumulative frequency of hindlimb scratching induced by intradermal injection of the NK-1 receptor specific agonist GR73632 in the Mongolian gerbil following oral administration of orvepitant maleate.

The present invention relates to the use of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt or a solvate thereof for the manufacture of a medicament for the treatment of pruritus.

2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide (otherwise known as orvepitant) has the following chemical structure (I).

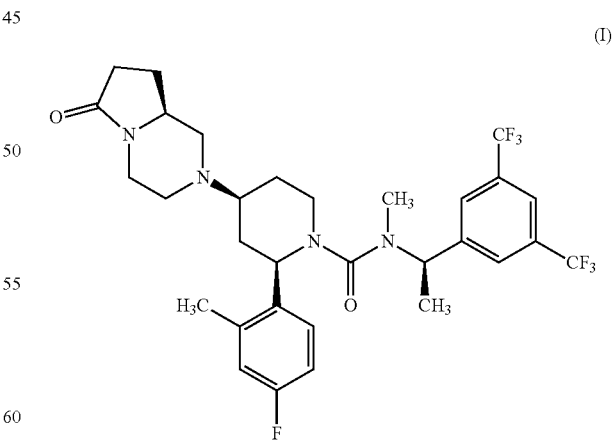

(I)

The compound (I) or its pharmaceutically acceptable salts may be prepared by the processes described in International patent applications no. WO2003/066635, WO2009/124996 and WO2007/048642, which are incorporated herein by reference.

Specifically, the Examples 9a and 11 of WO2003/066635 describe the synthesis of the compound (I) as free base and as hydrochloride salt respectively. Specific crystalline forms of hydrochloride salt namely anhydrous and dihydrate crystalline forms are described in the Examples 11a and 11b respectively. Example 11c describes the synthesis of the compound (I) as a maleate salt. Examples 2-8 of WO2009/124996 describe the synthesis of the maleate salt of the compound (I) as anhydrous crystalline form (Form1). Example 1 of WO2007/048642 discloses a process for preparing an intermediate in the synthesis of the compound (I).

It will be appreciated that for use in medicine, the salts of the compound (I) should be pharmaceutically acceptable. Suitable pharmaceutically acceptable salts will be apparent to those skilled in the art and include for example acid addition salts formed with pharmaceutically acceptable organic or inorganic acids. Examples of salts include hydrochloride, hydrobromide, sulphate, alkyl- or arylsulphonate e.g. methanesulphonate otherwise known as mesylates or p-toluenesulphonate (otherwise known as tosylate), phosphate, acetates, citrate, succinate, tartrate, fumarate and maleate.

One such pharmaceutically acceptable salt of the compound (I) for use according to the present invention is the maleate salt (orvepitant maleate).

Certain salts of the compound (I) may exist in stereoisomeric forms (e.g. they may contain one or more asymmetric carbon atoms). The individual stereoisomers (enantiomers and diastereomers) and mixtures of these are included within the scope of the present invention. Likewise, it is understood that salts of the compound (I) may exist in tautomeric forms and these are also included within the scope of the present invention.

The compound (I) may form acid addition salts with one or more equivalents of the acid. The present invention may employ all possible stoichiometric and non-stoichiometric forms thereof in the formulations of the invention.

The compound (I) or pharmaceutically acceptable salts thereof may exist in the form of a solvate.

It will be appreciated that many organic compounds can form complexes with solvents in which they are reacted or from which they are precipitated or crystallised. These complexes are known as "solvates". For example, a complex with water is known as a "hydrate". Solvents with high boiling points and/or solvents with a high propensity to form hydrogen bonds such as water, ethanol, iso-propyl alcohol, and N-methyl pyrrolidinone may be used to form solvates. Methods for the identification of solvated include, but are not limited to, NMR and microanalysis.

The compound (I) or pharmaceutically acceptable salts thereof may exist in different polymorphic forms.

Polymorphism is defined as the ability of an element or compound to crystallise in more than one distinct crystalline phase. Thus, polymorphs are distinct solids sharing the same molecular formula, however since the properties of any solid depends on its structure, different polymorphs may exhibit distinct physical properties such as different solubility profiles, different melting points, different dissolution profiles, different thermal and/or photostability, different shelf life, different suspension properties and different physiological absorption rate. Inclusion of a solvent in the crystalline solid leads to solvates, and in the case of water as a solvent, hydrates.

Included within the compound (I) are all solvates (including hydrates) and polymorphs of the compound (I) or pharmaceutically acceptable salts thereof.

The compound (I) or pharmaceutically acceptable salts or solvates thereof has now been determined to be useful in the treatment of pruritus.

According to IFSI in 2007 (Ständer S et al. *Acta Derm Venereol* (2007), 87:291-294), pruritus can be distinguished as acute and chronic, with the latter defined as pruritus lasting 6 or more weeks and it has been classified into the following groups:

Group I. Pruritus on primary diseased, inflamed skin.

Group II. Pruritus on primary non-diseased, non-inflamed skin.

Group III. Pruritus presenting with severe chronic secondary scratch lesions.

In one embodiment of the invention, the compound for use according to the present invention is 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate (orvepitant maleate).

In one embodiment of the invention, the compound for use according to the present invention is 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) (orvepitant maleate Form1).

All numbers expressing quantities, percentages or proportions, and other numerical values used in the specification and claims, are to be understood as being modified in all instances by the term "about."

It should be understood that the terms "a" and "an" as used herein refer to "one or more" of the enumerated components. It will be clear to one of ordinary skill in the art that the use of the singular includes the plural unless specifically stated otherwise.

As used herein, the terms "treatment," "treating," and the like, refer to obtaining a desired pharmacologic, physiologic, dermatologic or cosmetic effect. The effect may be prophylactic in terms of completely or partially preventing a condition or disease or disorder or symptom thereof and/or may be therapeutic in terms of a partial or complete cure for a condition or disease or disorder and/or adverse symptom or effect attributable to the condition or disease or disorder. "Treatment," thus, for example, covers any treatment of a condition or disease in a mammal, particularly in a human, and includes: (a) preventing the condition or disease, disorder or symptom thereof from occurring in a subject which may be predisposed to the condition or disease or disorder but has not yet been diagnosed as having it; (b) inhibiting the condition or disease, disorder or symptom thereof, such as, arresting its development; and (c) relieving, alleviating or ameliorating the condition or disease or disorder or symptom thereof, such as, for example, causing regression of the condition or disease or disorder or symptom thereof.

As used herein, the term "effective amount" means that amount of a drug or pharmaceutical agent that will elicit the biological or medical response of a tissue, system, animal or human that is being sought, for instance, by a researcher, clinician or veterinarian.

The term "pruritus" is known to the person skilled in the art. It is a condition characterised by an unpleasant skin sensation, leading to the desire to scratch.

As used herein, the term "pruritus" is interchangeable with the term "itch" and intended to have the same meaning.

As used herein, the term "pruritus" or "itch" unless otherwise stated includes both acute pruritus and chronic pruritus As used herein, the term "chronic pruritus" refers to pruritus lasting 6 or more weeks.

"Itch" or "pruritus" can be a symptom of many diseases, disease states, or disorders.

It may also be present independently of a disease, disease state, or disorder. The term "itch" or "pruritus" includes itch, or pruritus, wherein the cause of the itch or pruritus is associated with or due to a disorder, disease or disease state, and includes itch or pruritus wherein the cause or origin is not understood.

The term "associated with" includes cases wherein both pruritus and the disorder or disease are present, and a link between them is suspected but not proven.

"Itch or pruritus related disorder or disease" is known in the field. The term "itch or pruritus related disorder or disease" means itch or pruritus associated with or due to a disorder or disease.

Accordingly, "itch or pruritus related disorder or disease" means "pruritus or pruritus related disorder or disease", which means "pruritus associated with or due to a disorder or disease".

As used herein, "pharmaceutically acceptable excipient" or "pharmaceutically acceptable carrier" mean a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be pharmaceutically-acceptable eg of sufficiently high purity.

The term "combination" as used herein refers to either a fixed combination in one dosage unit form, or non-fixed combination.

The term "fixed combination" means that the active ingredients, e.g. a compound of formula (I) or pharmaceutically acceptable salt thereof and a combination partner, are both administered to a patient simultaneously in the form of a single entity or dosage.

The term "non-fixed combination" means that the active ingredients, e.g. a compound (I) or pharmaceutically acceptable salt thereof and a combination partner, (e.g. another drug as explained below, also referred to as "therapeutic agent" or "co-agent") are both administered to a patient as separate entities either simultaneously, concurrently or sequentially with no, specific time limits, wherein such administration provides therapeutically effective levels of the two compounds in the body of the patient. The latter also applies to cocktail therapy, e.g., the administration of three or more active ingredients.

The terms "co-administration" or "combined administration" or the like as utilized herein are meant to encompass administration of the compound (I) and the selected combination partner to a single subject in need thereof (e.g. a patient), and are intended to include treatment regimens in which the agents are not necessarily administered by the same route of administration or at the same time.

The patient to be treated using the invention described herein is preferably a human.

In an alternative embodiment, the invention provides for the veterinary treatment of non-human mammals.

In one embodiment of the present invention, pruritus is chronic pruritus.

In one embodiment of the present invention, pruritus is acute pruritus.

In one embodiment of the present invention, pruritus is of unknown or uncertain cause or origin.

In one embodiment of the present invention, pruritus is due to or associated with a disease or a disorder or a condition.

Pruritus, according to the present invention, includes pruritus on primary diseased, inflamed skin (Group I), pruritus on primary non-diseased, non-inflamed skin (Group II) or pruritus presenting with severe chronic secondary scratch lesions (Group III).

In one embodiment of the present invention, pruritus is associated with primary diseased inflamed skin (Group I).

In one embodiment of the present invention, pruritus is associated with primary non-diseased, non-inflamed skin (Group II).

In an embodiment of the present invention, pruritus is associated with severe chronic secondary scratch lesions (Group III).

In one embodiment of the invention, pruritus is associated with or due to a dermatological disorder, disease or condition (Category I) such as but not limited to:

Inflammatory dermatoses including atopic dermatitis/eczema, psoriasis, irritant/contact dermatitis, irritant/contact eczema, urticaria, dry skin, adverse drug reactions, scars, pruritus ani, pruritus scroti, pruritus vulvae and 'invisible dermatoses';

Infectious dermatoses including mycotic, bacterial and viral infections and folliculitis, scabies, pediculosis, arthropod reactions and insect bites;

Autoimmune dermatoses including bullous dermatoses, especially dermatitis herpetiformis Duhring, bullous pemphigoid and dermatomyositis;

Genodermatoses including Darier's disease, Hailey-Hailey disease, ichthyoses, Sjögren-Larsson syndrome and epidermolysis bullosa pruriginosa;

Dermatoses of pregnancy including polymorphic eruption of pregnancy, pemphigoid gestationis and prurigo gestationis;

Neoplasms including cutaneous T-cell-lymphoma (especially erythrodermic variants and Sézary syndrome and mycosis fungoides), cutaneous B-cell lymphoma and leukaemic infiltrates of the skin.

As used herein pruritus associated with or due to a dermatological diseases also include pruritus associated with or due to radiation dermatitis (also known as radiodermatitis) including acute and chronic radiation dermatitis, or due to cercarial dermatitis or Schistosome cercarial dermatitis or due to burn injuries or associated with scars such as for example pruritus found in keloid or hypertrophic scars for example following wound healing after either thermal or traumatic injury.

It has been also found that the compound (I) or pharmaceutically acceptable salts thereof can be effective in the treatment of certain skin diseases including Inflammatory dermatoses, such as for example dermatitis/eczema, psoriasis, irritant/contact dermatitis, irritant/contact eczema, radiation dermatitis (also known as radiodermatitis), cercarial dermatitis or Schistosome cercarial dermatitis, urticaria, dry skin, infectious dermatoses such as for example mycotic, bacterial and viral infections and folliculitis, scabies, pediculosis, arthropod reactions and insect bites; Autoimmune dermatoses such as for example bullous dermatoses, especially dermatitis herpetiformis Duhring, bullous pemphigoid and dermatomyositis; Genodermatoses including Darier's disease, Hailey-Hailey disease, ichthyoses, Sjögren-Larsson syndrome and epidermolysis bullosa pruriginosa; Dermatoses of pregnancy including polymorphic eruption of pregnancy, pemphigoid gestationis or prurigo gestationis.

Particularly, the topical use of compound (I) can be efficacious in the treatment of said skin diseases.

In one embodiment of the invention, pruritus is associated with or due to a systemic disorder, disease or condition (Category II) such as but not limited to:

Endocrine and metabolic diseases including chronic renal failure, liver diseases with or without cholestasis, hyperthyroidism, malabsorption, perimenopausal pruritus and diabetes mellitus;

Infectious diseases including HIV infection, HCV infection, chicken-pox, helminthosis and parasitosis;

Haematological and lymphoproliferative diseases including iron deficiency, polycythaemia vera, Hodgkin's disease, Non-Hodgkin's lymphoma and plasmocytoma;

Visceral neoplasms including solid tumours of the cervix, prostate, or colon and carcinoid syndrome;

Pregnancy including pruritus gravidarum with and without cholestasis;

Drug-induced pruritus such as opioids, ACE-inhibitors, amiodarone, hydrochlorothiazid, estrogens, simvastatin, hydroxyethyl starch, allopurinol or chemotherapy-induced pruritus.

As used herein chemotherapy-induced pruritus means pruritus in patients receiving anti-cancer drugs.

As used herein chemotherapy-induced pruritus includes but is not limited to targeted cancer therapy-induced pruritus.

As used herein "targeted cancer therapy-induced pruritus" means pruritus, including pruritus associated with cutaneous manifestations, in patients receiving drugs or other substances that block the growth and spread of cancer by interfering with specific cancer pathways, proteins or other molecules involved in tumor development and progression.

As used herein "targeted cancer therapy" includes but is not limited to epidermal growth factor receptor (EGFR) inhibitors including monoclonal antibodies such as for example erlotinib, gefitinib, panitumumab and cetuximab, dual inhibitors of EGFR and human epidermal growth factor receptor 2 (HER2) inhibitors such as for example lapatinib, neratinib, and afatinib, pan-growth factor receptor inhibitors such as for example dacomitinib, mammalian target of rapamycin (mTOR) inhibitors such as for example everolimus and temsirolimus, Bcr-Abl inhibitors such as for example dasatinib, imatinib, nilotinib, BRaf kinase inhibitors such as for example sorafenib, vemurafenib and dabrafenib, Dual EGFR vascular endothelial growth factor receptor (VEGFR) inhibitors such as for example vandetanib, MEK kinase inhibitors such as for example selumetinib and trametinib, multiple tyrosine kinase inhibitors such as for example sunitinib, monoclonal antibodies to CD20 such as for example rituximab and tositumomab; monoclonal antibodies to the programmed death receptor such as for example nivolumab and lambrolizumab or monoclonal antibodies to CTLA4 such as for example ipilimumab.

In one embodiment of the invention, pruritus is chemotherapy-induced pruritus.

In a further embodiment of the invention, pruritus is a targeted cancer therapy-induced pruritus.

In a further embodiment of the invention, pruritus is due to a targeted cancer therapy selected from epidermal growth factor receptor (EGFR) inhibitors, dual inhibitors of EGFR and human epidermal growth factor receptor 2 (HER2) inhibitors, pan-growth factor receptor inhibitors, mammalian target of rapamycin (mTOR) inhibitors, Bcr-Abl inhibitors, BRaf kinase, dual EGFR vascular endothelial growth factor receptor (VEGFR) inhibitors, MEK kinase inhibitors, multiple tyrosine kinase inhibitors, monoclonal antibodies to CD20, monoclonal antibodies to the programmed death receptor or monoclonal antibodies to CTLA4.

In a further embodiment of the invention, pruritus is due to a targeted cancer therapy selected from epidermal growth factor receptor (EGFR) inhibitors or dual inhibitors of EGFR and human epidermal growth factor receptor 2 (HER2) inhibitors.

In one embodiment of the invention, pruritus is associated with or due to a neurogenic disorder, disease or condition (Category III) such as for example:

Neurogenic origin (without neuronal damage) including hepatic itch with increased endogenous μ-opioids (dis-inhibition of itch);

Neuropathic diseases (neuronal damage causes itch) including multiple sclerosis, neoplasms, abscesses, cerebral or spinal infarcts, brachioradial pruritus, nostalgia paresthetica, post-herpetic neuralgia, vulvodynia and small fibre neuropathy.

In one embodiment of the invention, pruritus is associated with or due to a somatoform disorder, disease or condition (Category IV) such as: psychiatric or psychosomatic diseases including depression, anxiety disorders, obsessive-compulsive disorders, schizophrenia, tactile hallucinosis and fatigue.

In one embodiment of the invention, pruritus (Category V) is associated with or due to overlapping of disorders, diseases or conditions described in Categories I to IV.

In one embodiment of the invention, pruritus (Category VI) is associated with or due pruritus associated with or due to an unknown disorder, disease or condition.

In one embodiment of the present invention, the disorder or disease is selected from the group consisting of pruritus due to dermatological disorders.

In another embodiment of the present invention, the disorder or disease is selected from the group consisting of pruritus due to systemic disorders.

In another embodiment of the present invention, the disorder or disease is selected from the group consisting of pruritus due to neurogenic diseases.

In another embodiment of the present invention, the disorder or disease is selected from the group consisting pruritus due somatoform diseases.

In a different embodiment, the origin or cause of the pruritus is unknown.

In another embodiment, the present invention provides the compound (I) or pharmaceutically acceptable salts thereof for use in the treatment of pruritus.

The origin or cause of said pruritus may be known, uncertain or unknown, and the present invention includes the treatment of pruritus of any cause or origin.

As used in the present invention the term pruritus also includes pruritus due to burns including also sunburn or due to skin-grafts.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt thereof, for use in the treatment of pruritus.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate for use in the treatment of pruritus.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of pruritus.

In another embodiment, the present invention provides the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of chronic pruritus.

In another embodiment, the present invention provides the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of acute pruritus.

In another embodiment, the present invention provides the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate for use in the treatment of chronic pruritus.

In another embodiment, the present invention provides the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of chronic pruritus.

In another embodiment, the present invention provides the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate for use in the treatment of acute pruritus.

In another embodiment, the present invention provides the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of acute pruritus.

In another embodiment, the present invention provides the 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus due to or associated with a dermatological disease or disorder or condition.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus due to or associated with a dermatological disease or disorder selected from one or more of atopic dermatitis, psoriasis, urticaria and erythema, allergic contact eczema, allergic contact dermatitis, irritant dermatitis, irritant eczema, dermatitis gangrenosa, dermatitis herpetiformis, dry skin dermatitis, factitial dermatitis, perioral dermatitis, radiation-related disorders of the skin and subcutaneous tissue, stasis dermatitis, seborrheic dermatitis, diaper dermatitis, unspecified contact dermatitis, exfoliative dermatitis, dermatitis due to substances taken internally, other and unspecified dermatitis, prurigo nodularis, insect bites, scabies, pediculosis, lichen ruber planus, folliculitis, dry skin (xerosis cutis), 'invisible dermatoses', and mycotic, bacterial and viral infections and folliculitis, scabies, pediculosis, arthropod reactions and insect bites, bullous dermatoses, especially dermatitis herpetiformis Duhring, bullous pemphigoid and dermatomyositis, Darier's disease, Hailey-Hailey disease, ichthyoses, Sjögren-Larsson syndrome and epidermolysis bullosa pruriginosa, polymorphic eruption of pregnancy, pemphigoid gestationis and prurigo gestationis, cutaneous T-cell-lymphoma (especially erythrodermic variants and Sézary syndrome and mycosis fungoides), cutaneous B-cell lymphoma and leukaemic infiltrates of the skin.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus due to or associated with a systemic disorder, disease or condition.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus due to or associated with a systemic disorder, disease or condition selected from one or more of endocrine and metabolic diseases including chronic renal failure, liver diseases with or without cholestasis, hyperthyroidism, malabsorption, perimenopausal pruritus and diabetes mellitus; Infectious diseases including HIV infection, HCV infection, chicken-pox, helminthosis and parasitosis; Haematological and lymphoproliferative diseases including iron deficiency, polycythaemia vera, Hodgkin's disease, Non-Hodgkin's lymphoma and plasmocytoma; Visceral neoplasms including solid tumours of the cervix, prostate, or colon and carcinoid syndrome.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of chemotherapy-induced pruritus.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of targeted cancer therapy-induced pruritus.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus due to a targeted cancer therapy selected from from epidermal growth factor receptor (EGFR) inhibitors or dual inhibitors of EGFR and human epidermal growth factor receptor 2 (HER2) inhibitors.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus due to or associated with a neurogenic disorder, disease or condition.

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus due to or associated with a neurogenic disorder, disease or condition selected from neuropathic diseases (neuronal damage causes itch) including multiple sclerosis, neoplasms, abscesses, cerebral or spinal infarcts, brachioradial pruritus, nostalgia paresthetica, post-herpetic neuralgia, vulvodynia and small fibre neuropathy or pruritus of neurogenic origin (without neuronal damage) including hepatic itch with increased endogenous μ-opioids (dis-inhibition of itch).

In another embodiment, the present invention provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of the pruritus due to or associated with a somatoform disorder, diseases or condition, selected from one or more of depression, anxiety disorders, obsessive-compulsive disorders, schizophrenia, tactile hallucinosis and fatigue.

In another embodiment, the present invention, provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus associated with a. secondary scratch lesions due to the group of diseases selected from prurigo nodularis, lichenification, lichen simplex chronicus, and neurodermatitis circumscripta;

b. Inflammatory dermatoses including atopic dermatitis/eczema, psoriasis, irritant/contact dermatitis, irritant/contact eczema and urticaria;

c. Neoplasms including cutaneous T-cell-lymphoma (especially erythrodermic variants and Sézary syndrome and mycosis fungoides), cutaneous B-cell lymphoma and leukaemic infiltrates of the skin;

d. Systemic diseases including chronic renal failure and liver diseases with or without cholestasis;

e. Chemotherapy-induced pruritus including targeted cancer therapy-induced pruritus f. Pruritus associated with or due to psychiatric diseases including depression, anxiety disorders, obsessive-compulsive disorders and schizophrenia.

Prurigo nodularis is also called nodular prurigo, Hyde's Disease or Picker's nodules.

In another embodiment, the present invention, provides 2-(R)-(4-Fluoro-2-methyl-phenyl)-4-(5)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus associated with secondary scratch lesions due to the group of diseases selected from prurigo nodularis, lichenification, lichen simplex chronicus, and neurodermatitis circumscripta.

In another embodiment, the present invention, provides 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for use in the treatment of pruritus associated with or due to prurigo nodularis.

In a further embodiment, the invention provides a method of treatment pruritus which comprises administering to a human in need thereof an effective amount of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof.

In one embodiment there is provided the use of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof for the manufacture of a medicament for the pruritus.

In one embodiment there is provided the use of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate for the manufacture of a medicament for the pruritus.

In one embodiment there is provided the use of 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for the manufacture of a medicament for the pruritus.

In one embodiment, the invention provides a method of treatment of pruritus which comprises administering to a human in need thereof an effective amount 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or pharmaceutically acceptable salts thereof.

In one embodiment, the invention provides a method of treatment of pruritus which comprises administering to a human in need thereof an effective amount 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate.

In one embodiment, the invention provides a method of treatment of pruritus which comprises administering to a human in need thereof an effective amount 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1).

In one embodiment, the human is a pediatric patient.

Pharmaceutical compositions for use in accordance with the present invention may be formulated in a conventional manner for use in human and veterinary medicine using one or more pharmaceutically acceptable carriers or excipients.

Thus, the compound (I) and its pharmaceutically acceptable salts may be formulated for oral, buccal, parenteral, topical (including ophthalmic and nasal), depot or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycolate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the composition may take the form of tablets or formulated in conventional manner.

The compound (I) or its pharmaceutically acceptable salts may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for constitution with a suitable vehicle, e.g. sterile pyrogen-free water, before use.

The compound (I) or its pharmaceutically acceptable salts can be formulated for dermal administration.

Dermal administration may include topical application or transdermal administration. Transdermal application can be accomplished by suitable patches, emulsions, ointments, solutions, suspensions, pastes, foams, aerosols, lotions, creams or gels as is generally known in the art, specifically designed for the transdermal delivery of active agents, optionally in the presence of specific permeability enhancers. Topical compositions can likewise take one or more of these forms. One or more active compounds may be present in association with one or more non-toxic pharmaceutically acceptable auxiliaries such as excipients, adjuvants (e.g. buffers), carriers, inert solid diluents, suspending agents, preservatives, fillers, stabilizers, anti-oxidants, food additives, bioavailability enhancers, coating materials, granulating and disintegrating agents, binding agents etc., and, if desired, other active ingredients.

The pharmaceutical composition may be formulated, for example, for immediate release, sustained release, pulsed release, two or more step release, or depot or any other kind of release.

The manufacture of the pharmaceutical compositions according to the present subject matter may be performed according to methods known in the art and will be explained in further detail below. Commonly known and used pharmaceutically acceptable auxiliaries as well as further suitable diluents, flavorings, sweetening agents, coloring agents etc. may be used, depending on the intended mode of administration as well as particular characteristics of the active compound to be used, such as solubility, bioavailability etc.

Any non-toxic, inert, and effective topical, oral, etc. pharmaceutically acceptable carrier may be used to formulate the compositions described herein. Well-known carriers used to formulate other topical therapeutic compositions for administration to humans are useful in these compositions. Examples of these components that are well known to those of skill in the art are described in *The Merck Index*, Thirteenth Edition, Budavari et al., Eds., Merck & Co., Inc., Rahway, N.J. (2001); the CTFA (Cosmetic, Toiletry, and Fragrance Association) *International Cosmetic Ingredient Dictionary and Handbook*, Tenth Edition (2004); and the "Inactive Ingredient Guide", U.S. Food and Drug Administration (FDA) Center for Drug Evaluation and Research (CDER) Office of Management, January 1996, the contents of which are hereby incorporated by reference in their entirety. Examples of such useful cosmetically acceptable excipients, carriers and diluents include distilled water, physiological saline, Ringer's solution, dextrose solution, Hank's solution, and DMSO, which are among those suitable for use herein.

These additional other inactive components, as well as effective formulations and administration procedures, are well known in the art and are described in standard textbooks, such as *Goodman and Gillman's: The Pharmacological Bases of Therapeutics,* 8th Ed., Gilman et al. Eds. Pergamon Press (1990) and *Remington's Pharmaceutical Sciences,* 17th Ed., Mack Publishing Co., Easton, Pa. (1990), both of which are incorporated by reference herein in their entirety.

In an embodiment, the present topical compositions are formulated in a serum, a gel cream, a lotion, a cream, an ointment, a gel, an aerosol, a foam, a foamable liquid, a solution (solubilized system), a paste, a suspension, a dispersion, an emulsion, a skin cleanser, a milk, a mask, a solid stick, a bar (such as a soap bar), an encapsulated formulation, a microencapsulated formulation, microspheres or nanospheres or vesicular dispersions, or other cosmetically acceptable topical dosage form. In the case of vesicular dispersions, the vesicles may be composed of lipids, which can be of the ionic or nonionic type, or a mixture thereof. The formulation can comprise one or more of an aqueous formulation and/or an anhydrous formulation.

In another embodiment, the present topical cosmetic composition in accordance with the subject matter described herein can comprise or consist of an anhydrous formulation, an aqueous formulation, or an emulsion.

For intranasal administration, the compound (I) or its pharmaceutically acceptable salts may be formulated as solutions for administration via a suitable metered or unitary dose device or alternatively as a powder mix with a suitable carrier for administration using a suitable delivery device.

A proposed dose of the compound (I) is approximately 0.5 to 30 mg per day. Preferably, it is 1 to 30 mg per day, more preferably 2.5 to 30 mg per day.

In one embodiment, the dose of the compound (I) is 10 mg per day or 30 mg per day.

It will be appreciated that it may be necessary to make routine variations to the dosage, depending on the age and condition of the patient and the precise dosage will be ultimately at the discretion of the attendant physician or veterinarian. The dosage will also depend on the route of administration.

If desired, other therapeutic agents can be employed in conjunction with those provided in the above-described compositions. The amount of active ingredients that may be combined with the carrier materials to produce a single dosage form will vary depending upon the host treated, the nature of the disease, disorder, or condition, and the nature of the active ingredients.

The pharmaceutical compositions of the present invention may be given in a single dose or multiple doses daily.

In one embodiment, the compound (I) and its pharmaceutically acceptable salts is administered orally once daily.

In an embodiment, the present compositions may be topically applied once or multiple times per day. In an embodiment, the present compositions are topically applied from one to four times daily. For example, starting with once daily and progressing to more frequent applications, if needed, is one strategy.

In an embodiment, the present compositions are topically applied from one to six times daily, for example, in the morning, at noon, in the afternoon, and/or in the evening.

It is understood, however, that a specific dose level for any particular patient will vary depending upon a variety of factors, including the activity of the specific active agent; the age, body weight, general health, sex and diet of the patient; the time of administration; the rate of excretion; possible drug combinations; the severity of the particular condition being treated; and the form of administration. One of ordinary skill in the art would appreciate the variability of such factors and would be able to establish specific dose levels using no more than routine experimentation.

Pharmacokinetic parameters such as bioavailability, absorption rate constant, apparent volume of distribution, unbound fraction, total clearance, fraction excreted unchanged, first-pass metabolism, elimination rate constant, half-life, and mean residence time are well known in the art.

The optimal formulations can be determined by one skilled in the art depending upon considerations such as the particular ingredients and the desired dosage. See, for example, *Remington's Pharmaceutical Sciences*, 18th ed. (1990, Mack Publishing Co., Easton, Pa. 18042), pp. 1435-1712, and "Harry's Cosmeticology", 8th ed. (2000, Chemical Publishing Co., Inc., New York, N.Y. 10016), the disclosure of each of which is hereby incorporated by reference herein in its entirety. Such formulations may influence the physical state, stability, rate of in vivo release, and rate of in vivo clearance.

In particular, the ability to formulate compositions capable of long term storage, without pre-mixing or compounding requirements prior to application, are also contemplated. Specifically, the present compositions remain unexpectedly stable in storage for periods including between about 3 months and about 3 years, about 3 months and about 2.5 years, between about 3 months and about 2 years, between about 3 months and about 20 months, and alternately any time period between about 6 months and about 18 months.

Thus, in another aspect, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt thereof for use in the treatment of pruritus.

In another embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate, for use in the treatment of pruritus.

In another embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of pruritus.

In another embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate, for use in the treatment of chronic pruritus.

In a further embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt thereof for use in the treatment of chronic pruritus.

In another embodiment, the invention provides a pharmaceutical composition comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of chronic pruritus.

In another embodiment, the invention provides pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of pruritus.

In another embodiment, the invention provides pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of chronic pruritus.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate, for use in the treatment of pruritus.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate for use in the treatment of chronic pruritus.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of pruritus.

In another embodiment, the invention provides a pharmaceutical composition for oral administration comprising 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide maleate as anhydrous crystalline form (Form1) for use in the treatment of chronic pruritus.

It will be appreciated by those skilled in the art that the compound (I) or pharmaceutically acceptable salts thereof according to the invention may advantageously be used in combination with one or more other therapeutic agents, for instance with emollients, with topical anesthetics such as pramoxine, intravenous immunoglobulins, non-steroidal anti-inflammatory drugs (NSAIDs) such as ibuprofen, aspirin, diclofenac and tenoxicam, cyclooxygenase-2 (COX-2) inhibitors such as celecoxib, transient receptor potential (TRP) channel modulators such as TRPV-1 channel agonists such as capsaicin, TRPV-1 channel antagonists such as PAC-14028, TRPV-3 channel antagonists such as GRC 15300, TRPM-8 channel activators such as menthol and icilin, TRPA-1 channel activators such as carvacrol and inhibitors such as menthol and AP18, 'caine' anesthetics for example lidocaine, kappa-opioid receptor agonists such as nalfurafine, opioid receptor antagonists for example naltrexone and nalmefene, opioid receptor inverse agonists for example naloxone, monoamine-based anti-depressants such as doxepin, paroxetine, fluvoxamine, sertraline and mirtazapine, immune and inflammatory reaction suppressors such as lenalidomide and tranilast, GABA analogues for example gabapentin and pregabalin, GABA-A receptor modulators for example phenobarbital, 5HT-3 antagonists such as ondansetron, antibiotics such as rifampicin and roxithromycin, bile acids for example ursodeoxycholic acid and cholestyramine, herbal medicines for example herose, calcineurin inhibitors for example cyclosporine, pimecrolimus and tacrolimus, α2-adrenergic agonists for example clonidine, β-adrenergic antagonists such as propranolol, histamine-1 (H1)-receptor antagonists for example azelastine, fexofenadine mizolastine, loratadine and cetirizine, histamine (H2) receptor antagonists for example cimetidine, histamine-4 (H4)-receptor antagonists for example JNJ-7777120, agonists of the Type I interferon receptors (IFNAR1 and IFNAR2c) for example interferons-alpha and beta, agonists of the Type II interferon gamma-receptor IFNgammaR1 that leads to a complex of IFNgammaR1 and IFNgammaR2 for example interferon-gamma, endocannabinoid modulators for example inhibitors of fatty acid amide hydrolase (FAAH), cannabinoid-1 receptor agonists such as delta 9-tetrahydrocannabinol, cannabinoid-2 receptor agonists such as N-Palmitoylethanolamine, mast cell degranulation inhibitors for example cromolyn, agonists of the erythropoietin receptor for example erythropoietin, inosine monophosphate dehydrogenase inhibitors that prevent guanosine nucleotide synthesis upon which T- and B-lymphocytes are dependent for their proliferation, for example mycophenolate mofetil, glucocorticoid anti-inflammatory drugs for example prednisolone, alclometasone and betamethasone, corticosteroids for example hydrocortisone, anabolic steroids for example stanozolol, inhibitors of the tumour necrosis factor (TNF) receptor for example etanercept, leukotriene receptor antagonists for example montelukast and zafirlukast, serine protease inhibitors for example nafamostat mesilate and camostat mesilate; also including chymase inhibitors for example SUN13834, inhibitors of proteinase-activated receptor-2 (PAR-2) for example a neutralizing antibody and the PAR-2 antagonist FSLLRY, nerve growth factor (NGF) inhibitors and of the NGF receptor complex (tropomyosin-related kinase A [TrkA] and p75) for example the TrkA inhibitors AG879 and K252a, and the anti-NGF antibody tanezumab, inhibitors of acetylcholine release for example of botulinum toxin A, inhibitors of the TLR-7 receptor for example 2'-O-methyl-modified RNAs, antagonists of the gastrin-releasing peptide receptor for example RC-3095, inhibitors of the interleukin-(IL)-31 receptor complex (IL-31 receptor A [IL-31RA] with the α-subunit of oncostatin M receptor [OSMRβ]) and of its ligand the cytokine IL-31 for example the IL-31 antibody BMS-981164, antagonists of the chemoattractant receptors expressed on type 2 T-Cells (CRTH2) for example ARRY-005, prostanoid DP1 receptor agonists for example TS-022, inhibitors of Janus kinases (JAK) 1 and 2 for example ruxolitinib, phosphodiesterase-(PDE)-4 inhibitors for example apremilast, NK-1 and/or NK-2 or/and NK-3 antagonists or inhibitors of their cognate ligands NK-A and NK-B, inhibitors of SP for example an anti-SP antibody, agonists of the vitamin D3 receptor for example calcipotriol.

In one embodiment, the present invention provides a combination which comprises (a) 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methylamide or a pharmaceutically acceptable salt thereof and (b) a second drug substance and optionally one or more pharmaceutically acceptable excipient(s) for the treatment of pruritus.

In a further embodiment, the present invention provides a combination of the compound(I) or a pharmaceutically acceptable salt thereof with a second drug substance which is selected from a H1 receptor antagonist, a H2 receptor antagonist, a H4 receptor antagonist, steroid, a TRP channel modulator, an opioid receptor agonist or antagonist, a calcineurin inhibitor, a GABA analogue, a gastrin-releasing peptide receptor antagonist, a proteinase-activated receptor-2 inhibitor, a cannabinoid receptor agonist, a nerve growth factor (NGF) inhibitor and of the NGF receptor complex and optionally one or more pharmaceutically acceptable excipient(s) for the treatment of pruritus.

In a further embodiment, the present invention provides a combination of the compound (I) or a pharmaceutically acceptable salt thereof with a second drug substance which is selected from H1 receptor antagonists and optionally one or more pharmaceutically acceptable excipient(s) for the treatment of pruritus.

H1 receptor antagonists which may be used in combination with the compound (I) or pharmaceutically salts thereof include but are not limited to azelastine, fexofenadine, mizolastine, loratadine and cetirizine.

In a further embodiment, the present invention provides a combination of the compound (I) or a pharmaceutically acceptable salt thereof with a second drug substance which is selected from H2 receptor antagonists and optionally one or more pharmaceutically acceptable excipient(s) for the treatment of pruritus.

H2 receptor antagonists which may be used in combination with the compound (I) or pharmaceutically salts thereof include but are not limited to cimetidine.

In a further embodiment, the present invention provides a combination of the compound (I) or a pharmaceutically acceptable salt thereof with a second drug substance which is selected from, a H4 receptor antagonist and optionally one or more pharmaceutically acceptable excipient(s) for the treatment of pruritus.

H4 receptor antagonists which may be used in combination with the compound (I) or pharmaceutically salts thereof include but are not limited to JNJ-7777120.

In a further embodiment, the present invention provides a combination of the compound (I) or a pharmaceutically acceptable salt thereof with a second drug substance which is selected from a steroid and optionally one or more pharmaceutically acceptable excipient(s) for the treatment of pruritus.

Steroids which may be used in combination with the compound (I) or pharmaceutically salts thereof include but are not limited to glucocorticoids for example prednisolone, alclometasone and betamethasone and corticosteriods for example hydrocortisone.

In a further embodiment, the present invention provides a combination of the compound (I) or a pharmaceutically acceptable salt thereof with a second drug substance which is selected from TRP channel modulators and optionally one or more pharmaceutically acceptable excipient(s) for the treatment of pruritus.

TRP channel modulators which may be used in combination with the compound (I) or pharmaceutically salts thereof include but are not limited to TRPV-1 channel agonists such as capsaicin, TRPV-1 channel antagonists such as PAC-14028, TRPV-3 channel antagonists such as GRC 15300, TRPM-8 channel activators such as menthol and icilin, TRPA-1 channel activators such as carvacrol or inhibitors such as menthol and AP18.

In a further embodiment, the present invention provides a combination of the compound (I) or a pharmaceutically acceptable salt thereof with a second drug substance which is selected from an opioid receptor agonist and antagonist and optionally one or more pharmaceutically acceptable excipient(s) for the treatment of pruritus.

Opioid receptor agonists which may be used in combination with the compound (I) or pharmaceutically salts thereof include but are not limited nalfurafine and naloxone.

Opioid receptor antagonists which may be used in combination with the compound (I) or pharmaceutically salts thereof include but are not limited to naltrexone and nalmefene.

In a further embodiment, the present invention provides a combination of the compound (I) or a pharmaceutically acceptable salt thereof with a second drug substance which is selected from a calcineurin inhibitor and optionally one or more pharmaceutically acceptable excipient(s) for the treatment of pruritus.

Calcineurin inhibitors which may be used in combination with the compound (I) or pharmaceutically salts thereof include but are not limited to cyclosporine, pimecrolimus and tacrolimus.

In a further embodiment, the present invention provides a combination of the compound (I) or a pharmaceutically acceptable salt thereof with a second drug substance which is selected from a GABA analogue and optionally one or more pharmaceutically acceptable excipient(s) for the treatment of pruritus.

GABA analogues which may be used in combination with the compound (I) or pharmaceutically salts thereof include but are not limited to gabapentin and pregabalin.

In a further embodiment, the present invention provides a combination of the compound (I) or a pharmaceutically acceptable salt thereof with a second drug substance which is selected from a gastrin-releasing peptide receptor antagonist and optionally one or more pharmaceutically acceptable excipient(s) for the treatment of pruritus.

Gastrin-releasing peptide receptor antagonists which may be used in combination with the compound (I) or pharmaceutically salts thereof include but are not limited to RC-3095.

In a further embodiment, the present invention provides a combination of the compound (I) or a pharmaceutically acceptable salt thereof with a second drug substance which is selected from a PAR-2 inhibitor and optionally one or more pharmaceutically acceptable excipient(s) for the treatment of pruritus.

PAR-2 inhibitor which may be used in combination with the compound (I) or pharmaceutically salts thereof include but are not limited to FSLLRY.

In a further embodiment, the present invention provides a combination of the compound (I) or a pharmaceutically acceptable salt thereof with a second drug substance which is selected from a cannabinoid receptor agonist and optionally one or more pharmaceutically acceptable excipient(s) for the treatment of pruritus.

Canabinnoid receptor agonists which may be used in combination with the compound (I) or pharmaceutically salts thereof include but are not limited to delta 9-tetrahydrocannabinol, and N-Palmitoylethanolamine.

In a further embodiment, the present invention provides a combination of the compound (I) or a pharmaceutically acceptable salt thereof with a second drug substance which is selected from a NGF inhibitor and of the NGF receptor complex and optionally one or more pharmaceutically acceptable excipient(s) for the treatment of pruritus.

NGF inhibitors and of the NGF receptor complex which may be used in combination with compound (I) or pharmaceutically salts thereof include but are not limited to AG879 and K252a.

In a further embodiment, the present invention provides a combination of the compound (I) or a pharmaceutically acceptable salt thereof with a second drug substance which is selected from a targeted cancer therapy and optionally one or more pharmaceutically acceptable excipient(s) for the treatment of pruritus.

In a further embodiment, the present invention provides a combination of the compound (I) or a pharmaceutically acceptable salt thereof with a second drug substance which is a phosphatase inhibitor and optionally one or more pharmaceutically acceptable excipient(s) for the treatment of pruritus.

Phosphatase inhibitors which may be used in combination with the compound (I) or pharmaceutically salts thereof include but are not limited to menadione (Vitamin K3).

The following examples illustrate the invention without limiting the scope thereof.

EXAMPLES

Pharmacological Activities

Preclinical Studies

The antipruritic effect of orvepitant maleate can be assessed for example in one or more animal models of pruritus by counting the number of scratching events over time, a quantitative measure of itch response can be made as described here below.

1) Reduction in scratching behaviour in a NC/Nga dermatitis mouse model as described in Tanaka A & Matsuda H. Evaluation of itch by using NC/NgaTnd mice: a model of human atopic dermatitis. *J Biomed Biotechnol.* (2010), 790436.

A pruritic dermatitis phenotype, with features that reproduce atopic dermatitis, arises spontaneously in NC/Nga mice or may be induced in this murine strain by repeated applications of haptens such as picryl chloride (also called TNCB). orvepitant maleate is administered to treated NC/Nga once a day in a range of doses versus un-treated mice.

2) Reduction in scratching in a hapten-induced pruritic dermatitis hairless mouse model as described in Ueda Y et al. A new chronic itch model accompanied by skin lesions in hairless mice. *Int Immunopharmacol* (2006), 6(10):1609-1615.

orvepitant maleate is administered to hairless mice treated with a hapten such TCNB to induce pruritic dermatitis, once a day in a range of doses versus un-treated mice.

3) Reduction in scratching in a flea-induced allergic dermatitis dog model as described in Bonneau S et al. Therapeutic efficacy of topical hydrocortisone aceponate in experimental flea-allergy dermatitis in dogs. *Aust Vet J.* (2009), 87(7):287-291.

orvepitant maleate is administered to dogs with flea-induced allergic dermatitis once a day in a range of doses versus un-treated dogs.

4) Reduction in scratching behaviour in a toluene-2,4-diisocyanate (TDI) induced allergic dermatitis model that shows persistent scratching in mice as described in Fuchibe K et al. Delayed type allergic itch-associated response induced by toluene-2,4-diisocyanate in hairless mice. *J Pharmacol Sci.* (2003), 93(1):47-54.

Orvepitant maleate is administered to mice with TDI-induced allergic dermatitis once a day in a range of doses versus un-treated mice.

5) Particularly the antipruritic effect of orvepitant maleate was determined in GR73632-induced scratching behaviour in the Mongolian gerbil. According to this metholody the scratching behaviour was induced by GR73632 which is a specific agonist of the NK-1 receptor.

MATERIALS

The abbreviations used in the examples unless otherwise specified are as follows:
ANOVA Analysis of Variance
cm centimeter
DMSO Dimethylsuphoxide
g gram
HCl Hydrochloric acid
HPMC Hydroxypropyl methycellulose
hr hour
i.d. intradermal
mg/kg Milligrams of compound per kilogram of animal
min Minute
ml milliliter
ml/kg Milliliters of solution per kilogram of animal
n Number
nmol nanomole
p.o. per os (oral)
s second
s.c. subcutaneous
s.e.m. Standard Error of the Mean
v/v Volume for volume
w/v Weight for volume
ul microliter
Animals 72 male Mongolian gerbils (58-78 g) after a minimum habituation period of 10 days prior to study commencement, were acclimatised to the procedure room in their home cages, with food and water available ad libitum. The day before the experiment was due to commence a 1 cm×1 cm squared area between the shoulder blades was shaved free of hair.

Habituation to the apparatus (custom made observation chambers; approximately 30×30 cm; 2 animals per observation) took place 30 minutes prior to induction of scratching behaviours using GR73632.

Vehicle Preparation

5% DMSO & 95% HPMC was made by addition of 5 mls DMSO to 95 mls of 0.5% HPMC. 0.5% HPMC was made by adding 1.5 g HPMC to 300 ml water.

Preparation of GR73632 Solutions 100 nmol stock solution of GR73632 was made by dissolving 1 mg of GR73632 in 1,305 uL saline to give a solution of 1305 nmol/1305 uL=100 nmol/100 uL.

From this solution 30 nmol was made by a 1:3.33 dilution (e.g. 1,050 uL of 100 nmol:2,450 uL saline=30 nmol/100 ul).

The dose of GR73632 (30 nmol/100 ul) used was determined to produce a significant scratching response in an initial dose response analysis.

Preparation of Orvepitant Maleate Solutions

A 10 mg/kg stock solution of orvepitant maleate was made by dissolving 20 mg of orvepitant maleate Form 1 in 20 mls of vehicle (5% DMSO & 95% HPMC (0.5%)). This stock solution was serially diluted to prepare doses of 0.1, 0.3, 1.0, 3.0 or 10 mg/kg orvepitant maleate.

Experimental Protocol

The experimental protocol is reported in Table 1.

At T=−60 mins mongolian gerbils were dosed with orvepitant maleate (0.1, 0.3, 1.0, 3.0 or, 10 mg/kg p.o.). Gerbils were allocated to dosing groups based on a Latin square design. 30 Minutes later (T=−30 mins) gerbils were placed into the observation chamber for 30 minutes habituation. At T=0 Gerbils were then dosed with GR73632 (30 nmol/100 uL; i.d.) between the shoulder blades and their subsequent hindlimb scratching behaviour recorded using GeoVision surveillance software over a 30 minute period.

TABLE 1

| Time (mins) | Test Article | Dose Level (mg/kg) | Dose Volume/ Route | No of Animals |
|---|---|---|---|---|
| −60 + | Vehicle + | — | 10 ml/kg p.o. | 12 |
| 0 | GR737632 | 30 nmol | 100 ul/i.d. | |
| −60 + | orvepitant maleate + | 0.1 | 10 ml/kg p.o. | 12 |
| 0 | GR737632 | 30 nmol | 100 ul/i.d. | |
| −60 + | orvepitant maleate + | 0.3 | 10 ml/kg p.o. | 12 |
| 0 | GR737632 | 30 nmol | 100 ul/i.d. | |
| −60 + | orvepitant maleate + | 1 | 10 ml/kg p.o. | 12 |
| 0 | GR737632 | 30 nmol | 100 ul/i.d. | |
| −60 + | orvepitant maleate + | 3 | 10 ml/kg p.o. | 12 |
| 0 | GR737632 | 30 nmol | 100 ul/i.d. | |
| −60 + | orvepitant maleate + | 10 | 10 ml/kg p.o. | 12 |
| 0 | GR737632 | 30 nmol | 100 ul/i.d. | |

RESULTS

Behavioural Assessment:

Playing back of the video served for counting scratching behaviour. The gerbils generally showed several rapid scratching movements by the hindpaws lasting for about 1 sec and this was scored as one bout. Cumulative frequency and duration (secs) of scratching was scored in 5 min epochs. Treatment groups were randomised based on a Latin Square design. The experimenter was blinded to the treatment groups.

The results of Cumulative frequency of hindlimb scratching are summarised in Table 2 and FIG. 1.

Figure 2:
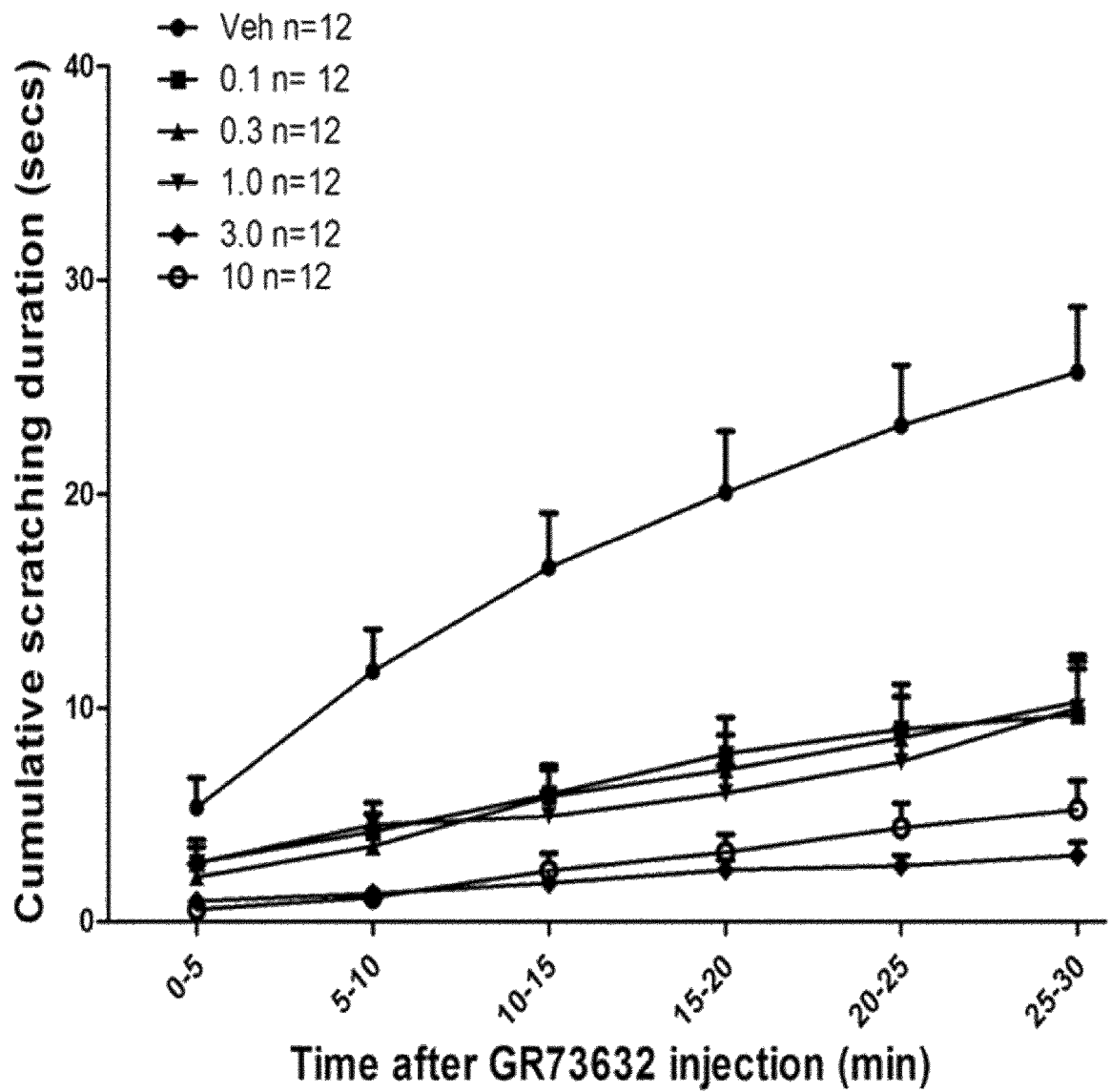
FIG. 2. Cumulative duration of hindlimb scratching induced by intradermal injection of the NK-1 receptor specific agonist GR73632 in the Mongolian gerbil following oral administration of orvepitant maleate.

The results of Cumulative duration of hindlimb scratching are summarised in Table 3 and FIG. 2.

Statistical Analysis

Repeated measures ANOVA followed by Planned comparison test using GraphPad Prism. ($p < 0.05$ considered significant). Data were analysed by comparing treatment groups to control group at each time point.

TABLE 2

Cumulative frequency of hindlimb scratching

| | | Dose of orvepitant maleate mg/kg p.o. | | | | |
|---|---|---|---|---|---|---|
| Time (mins) | Vehicle | 0.1 | 0.3 | 1.0 | 3.0 | 10.0 |
| 0-5 | 7.75 ± 2.18 | NS4.08 ± 1.45 | NS3.00 ± 0.88 | NS3.75 ± 1.30 | NS1.58 ± 0.46 | *0.91 ± 0.43 |
| 5-10 | 14.41 ± 2.49 | **5.83 ± 1.55 | ***4.91 ± 1.15 | ***5.91 ± 1.25 | ***2.16 ± 0.58 | ***1.66 ± 0.60 |

TABLE 2-continued

Cumulative frequency of hindlimb scratching

| | Dose of orvepitant maleate mg/kg p.o. | | | | | |
|---|---|---|---|---|---|---|
| Time (mins) | Vehicle | 0.1 | 0.3 | 1.0 | 3.0 | 10.0 |
| 10-15 | 20.25 ± 2.97 | ***7.91 ± 1.74 | ***7.50 ± 1.56 | ***6.41 ± 1.29 | ***2.83 ± 0.57 | ***2.58 ± 0.73 |
| 15-20 | 24.33 ± 3.22 | ***9.66 ± 1.92 | ***8.66 ± 1.61 | ***8.00 ± 1.39 | ***3.66 ± 0.64 | ***3.58 ± 0.73 |
| 20-25 | 28.25 ± 3.26 | ***10.91 ± 2.07 | ***10.00 ± 1.62 | ***9.66 ± 1.71 | ***4.00 ± 0.67 | ***5.00 ± 0.92 |
| 25-30 | 32.00 ± 3.60 | ***11.58 ± 2.12 | ***11.75 ± 1.90 | ***12.08 ± 2.25 | ***4.58 ± 0.76 | ***5.91 ± 1.16 |

*$p < 0.05$,
**$p < 0.01$ and
***$p < 0.001$.
Values are meant ± s.e.m.

TABLE 3

Cumulative duration of hindlimb scratching

| Time | Dose- of orvepitant maleate mg/kg p.o. | | | | | |
|---|---|---|---|---|---|---|
| (mins) | Vehicle | 0.1 | 0.3 | 1.0 | 3.0 | 10.0 |
| 0-5 | 5.35 ± 1.37 | NS 2.76 ± 0.71 | NS 2.06 ± 0.62 | NS 2.74 ± 1.06 | NS 0.96 ± 0.32 | NS 0.57 ± 0.29 |
| 5-10 | 11.71 ± 1.93 | **4.20 ± 0.85 | **3.50 ± 0.88 | **4.51 ± 1.05 | ***1.30 ± 0.38 | ***1.13 ± 0.38 |
| 10-15 | 16.54 ± 2.58 | ***5.96 ± 1.16 | ***5.86 ± 1.44 | ***4.92 ± 1.13 | ***1.79 ± 0.39 | ***2.38 ± 0.78 |
| 15-20 | 20.08 ± 2.83 | ***7.86 ± 1.67 | ***7.09 ± 1.63 | ***6.02 ± 1.28 | ***2.415 ± 0.47 | ***3.22 ± 0.84 |
| 20-25 | 23.19 ± 2.80 | ***8.99 ± 2.09 | ***8.58 ± 1.93 | ***7.48 ± 1.55 | ***2.59 ± 0.50 | ***4.36 ± 1.18 |
| 25-30 | 25.69 ± 3.026 | ***9.67 ± 2.14 | ***10.27 ± 2.17 | ***10.00 ± 2.17 | ***3.09 ± 0.61 | ***5.24 ± 1.35 |

*$p < 0.05$,
**$p < 0.01$ and
***$p < 0.001$.
Values are meant ± s.e.m.

The above results have shown that Orvepitant produced a profound inhibition of GR73632 induced hindlimb scratching at all doses tested (from 0.1 to 10.0 mg/kg).

Clinical Studies

1. The Itch-Mitigating Effect Orvepitant with Patients with Previously Diagnosed Prurigo Nodularis The efficacy of orvepitant maleate as an antipruritic agent is evaluated in a 6 week, placebo controlled study in patients presenting chronic (>6 weeks duration) and severe (visual analogue scale (VAS) score ≥7) pruritus of multifactorial origin who have atopic diathesis and are suffering from secondary scratch lesions arising from their primary disease manifesting as prurigo nodularis. Efficacy is assessed as the difference between the test compound arm and placebo, in the change from baseline of the VAS score. Secondary endpoints will include the Dermatology Quality of Life Index (DQL I) together with assessment of insomnia and depressive symptoms.

VAS is a patient assessed pruritus intensity scoring scale that ranges from '0=no pruritis to '10=very severe pruritus'. Reich A et al. Visual Analogue Scale: Evaluation of the Instrument for the Assessment of Pruritus. *Acta Derm Venereol* (2012), 92:497-501. DQLI is a 10-question validated questionnaire to evaluate the impact of a treatment on patient quality of life. Finlay A Y & Khan G K. Dermatology Life Quality Index (DLQI)-a simple practical measure for routine clinical use. *Clin Exp Dermatol* (1994), 19(3):210-6.

The clinical study provides information regarding the anti-pruritic effect of the test compound, both acutely and for longer-term maintenance, as well as an indication of the healing effect on the nodular scratch lesions.

2. The Itch-Mitigating Effect Orvepitant with Patients Undergoing Treatment with an Targeted Cancer Therapy for Example an EGFR Inhibitor (EGFRi) or Dual EGFRi/HER2 Inhibitor.

The efficacy of orvepitant maleate as an antipruritic agent is evaluated in a 8 week, double-blind placebo controlled study in subjects with a diagnosis of malignant solid tumours and undergoing treatment with one of the following EGFRi medicines: cetuximab, panitumumab, erlotinib, or gefitinib or a dual EGFRi-HER2 inhibitor therapy lapatinib, that induce intense pruritus symptoms as defined by subjects reporting a baseline clinic visit Numerical Rating Scale (NRS) score ≥7, (where 0=No Itch and 10=Worst Itch Imaginable)

Efficacy is assessed as the difference between the test compound arms and placebo, in the change from baseline of the subject-recorded NRS score at the primary endpoint. Secondary endpoints will include the change from baseline in both the Skindex-16 Quality of Life scale and in the Leeds Sleep Evaluation Questionnaire (LSEQ) to assess insomnia symptoms.

Pharmaceutical Compositions

Orvepitant maleate Form 1 will normally, but not necessarily, be formulated into pharmaceutical compositions prior to administration to a patient. In one aspect, the invention is directed to pharmaceutical compositions comprising orvepitant maleate Form 1.

Tablets of orvepitant maleate Form 1 have been formulated as white to off-white, film-coated round tablets containing 10 mg, 30 mg, 50 mg and 60 mg of orvepitant which provide an immediate release of the active ingredient for oral administration.

The list of excipients and quantitative composition of tablets are reported in Table 4 below.

TABLE 4

Composition of Tablets Orvepitant Maleate Form 1

| Component | Quantity (mg/tablet) | | | | Function |
| --- | --- | --- | --- | --- | --- |
| | 10 mg | 30 mg | 50 mg | 60 mg | |
| Tablet core | | | | | |
| Orvepitant maleate Form1 | 11.85[1] | 35.54[2] | 59.23[3] | 71.09[4] | Active |
| Microcrystalline cellulose | 60.00 | 149.22 | 60.00 | 79.39 | Filler |
| Lactose monohydrate | 201.90 | 95.54 | 154.52 | 122.12 | Filler |
| Croscarmellose sodium | 9.00 | 5.92 | 9.00 | 11.85 | Disintegrant |
| Hypromellose | 15.00 | 10.78 | 15.00 | 12.55 | Binder |
| Magnesium stearate | 2.25 | 3.00 | 2.25 | 3.00 | Lubricant |
| Purified water[5] | qs | qs | qs | qs | Granulating fluid |
| Total unit dose | 300.00 | 300.0 | 300.00 | 300.0 | — |
| Coat | | | | | |
| Opadry ® White OY-S-28876 | 9.00 | 9.0 | 9.00 | 9.0 | Coating agent |
| Purified water[5] | qs | qs | qs | qs | Suspending agent |

Note:
[1]Corresponding to 10.0 mg as orvepitant
[2]Corresponding to 30.0 mg as orvepitant
[3]Corresponding to 50.0 mg as orvepitant
[4]Corresponding to 60.0 mg as orvepitant
[5]Removed during processing. Does not appear in the final product.

Orvepitant maleate tablets, 10 mg, 30 mg, 50 mg and 60 mg were manufactured using wet granulation, dry blending, tablet compression and film coating processes.

Drug substance, lactose monohydrate, microcrystalline cellulose and croscarmellose sodium were sieved and dry mixed into the high shear mixer granulator for approximately 5 minutes. The granulation water was sprayed onto the drug substance, lactose monohydrate, microcrystalline cellulose and croscarmellose sodium dry blend. The wet granule was dried approximately at 65° C. into a fluid bed dryer for approximately 45 minutes (<2% LOD), milled using a conical mill (screen size 813 μm) and blended into a bin blender with lactose monohydrate, microcrystalline cellulose and croscarmellose sodium for approximately 20 minutes. Magnesium stearate was added for lubrication into the bin blender and the mixture was blended for approximately 3 minutes.

The blend was compressed using a suitable rotary tablet compression machine to obtain uncoated tablets. Opadry® White OY-S-28876 was charged into a mixing vessel with purified water and the film coating suspension prepared with stirring. The tablets were film coated into a suitable pan coater (approximately 3% weight gain).

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way.

The invention claimed is:

1. A method of treatment of chronic pruritus, wherein the pruritus is due to or associated with inflammatory dermatoses selected from atopic dermatitis/eczema, psoriasis, irritant/contact dermatitis, irritant/contact eczema, urticarial, dry skin, adverse drug reactions, scars, pruritus ani, pruritus scroti, pruritus vulvae and invisible dermatosis said method comprising
administering to a human in need thereof 2-(R)-(4-Fluoro-2-methyl-phenyl)-4-(S)-((8aS)-6-oxo-hexahydro-pyrrolo[1,2-a]-pyrazin-2-yl)-piperidine-1-carboxylic acid [1-(R)-(3,5-bis-trifluoromethyl-phenyl)-ethyl]-methyl-amide or a pharmaceutically acceptable salt thereof.

2. A method of treatment according to claim 1, wherein the pharmaceutically acceptable salt of the compound is maleate.

3. A method of treatment according to claim 1, wherein the compound is orvepitant maleate as anhydrous crystalline form.

4. A method according to claim 1, wherein inflammatory dermatoses is selected from atopic dermatitis/eczema.

5. A method of treatment according to claim 1, wherein the compound is orvepitant maleate as anhydrous crystalline form characterized in that it provides an X-ray powder diffraction (XRD) pattern expressed in terms of 2 theta angles and obtained with a diffractometer using copper K X-radiation, wherein the XRD pattern comprises 2 theta angle peaks at essentially at 7.30.1, 7.50.1, 10.90.1, 12.70.1, 16.50.1 degrees, which correspond respectively to d-spacings at 12.2, 11.8, 8.1, 7.0 and 5.4 Angstroms (Å).

* * * * *